(12) United States Patent
Sanders et al.

(10) Patent No.: US 12,349,882 B2
(45) Date of Patent: Jul. 8, 2025

(54) DUAL CHECK VALVE ONE HANDED APPLICATOR

(71) Applicants: Baxter International Inc., Deerfield, IL (US); Baxter Healthcare SA, Glattpark (CH)

(72) Inventors: Paul J. Sanders, Greendale, WI (US); Krishnakumarsinh Hitendrasinh Parmar, Lisle, IL (US); Jerome Schafer, Liberty Township, OH (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 931 days.

(21) Appl. No.: 17/291,880

(22) PCT Filed: Nov. 7, 2018

(86) PCT No.: PCT/US2018/059628
§ 371 (c)(1),
(2) Date: May 6, 2021

(87) PCT Pub. No.: WO2020/096587
PCT Pub. Date: May 14, 2020

(65) Prior Publication Data
US 2022/0015749 A1  Jan. 20, 2022

(51) Int. Cl.
*A61B 17/00* (2006.01)
*A61B 17/34* (2006.01)
*A61L 24/10* (2006.01)

(52) U.S. Cl.
CPC .... *A61B 17/00491* (2013.01); *A61B 17/3498* (2013.01); *A61L 24/104* (2013.01);
(Continued)

(58) Field of Classification Search
CPC ............... A61B 17/00491–2017/00495; A61B 17/3498; A61B 2017/00407;
(Continued)

(56) References Cited

U.S. PATENT DOCUMENTS 6,047,861 A * 4/2000 Vidal ............... A61B 17/00491
222/391
6,079,868 A * 6/2000 Rydell ................... A61F 2/441
604/416
(Continued)

FOREIGN PATENT DOCUMENTS

CA 2295249 A1 7/2001
CN 102958455 A 3/2013
(Continued)

OTHER PUBLICATIONS

International Search Report for related International Application No. PCT/US2018/059628; action dated May 14, 2020; (6 pages).
(Continued)

*Primary Examiner* — Brigid K Byrd
(74) *Attorney, Agent, or Firm* — K&L Gates LLP (57) ABSTRACT

Delivery devices, delivery systems, and related methods, for precise administration of hemostatic compositions are disclosed, which may include a trigger mechanism, a pusher, a valve, and a cannula. The pusher is configured to engage with the trigger mechanism, retain a first syringe, a least by coupling with a plunger of the first syringe. The valve is fluidly coupled to the first syringe. The valve is further configured to engage with a second syringe, in fluid communication with both the valve and the first syringe. The cannula extends distally from and is fluidly coupled to the valve. Activation of the trigger mechanism causes the pusher and the plunger of the first syringe to translate in a distal direction, to expel a composition out of the first syringe,
(Continued)

through the valve, through the cannula, and out of a distal end of the cannula.

6 Claims, 7 Drawing Sheets

(52) U.S. Cl.
CPC .............. *A61B 2017/00407* (2013.01); *A61B 2017/0042* (2013.01); *A61B 2017/00495* (2013.01); *A61B 2017/00884* (2013.01); *A61L 2300/418* (2013.01); *A61L 2400/04* (2013.01)

(58) Field of Classification Search
CPC .. A61B 2017/0042; A61B 2017/00884; A61L 24/104; A61L 2300/418; A61L 2400/04
See application file for complete search history.

(56) References Cited

U.S. PATENT DOCUMENTS

| | | | |
|---|---|---|---|
| 2002/0077589 A1* | 6/2002 | Tessari | B01F 33/50112 604/82 |
| 2005/0092387 A1 | 5/2005 | Schorn et al. | |
| 2008/0188843 A1 | 8/2008 | Appling et al. | |
| 2008/0269720 A1* | 10/2008 | Sabbah | A61B 17/12195 604/522 |
| 2009/0247985 A1* | 10/2009 | Melsheimer | A61J 1/2096 604/506 |
| 2010/0310782 A1* | 12/2010 | Wawrzyniak | A61B 17/00491 118/612 |
| 2011/0319930 A1 | 12/2011 | Roush et al. | |
| 2012/0065502 A1 | 3/2012 | Levy et al. | |
| 2012/0143206 A1 | 6/2012 | Wallace et al. | |
| 2013/0211374 A1 | 8/2013 | Hetherington | |
| 2015/0025500 A1 | 1/2015 | Piehl et al. | |
| 2015/0297207 A1 | 10/2015 | Maxwell et al. | |
| 2016/0166761 A1* | 6/2016 | Piehl | A61B 17/3498 604/207 |

FOREIGN PATENT DOCUMENTS

| | | |
|---|---|---|
| CN | 103596619 A | 2/2014 |
| CN | 104159625 A | 11/2014 |
| JP | 2007530139 A | 11/2007 |
| JP | 2011104443 A2 | 6/2011 |
| JP | 2012161473 A2 | 3/2015 |
| JP | 5781597 B2 | 9/2015 |
| JP | 2017177073 A2 | 10/2017 |
| WO | 9944509 A1 | 9/1999 |
| WO | 2010129747 A1 | 11/2010 |
| WO | 2013098806 A1 | 7/2013 |
| WO | 2016138018 A2 | 9/2016 |

OTHER PUBLICATIONS

Written Opinion for related International Application No. PCT/US2018/059628; action dated May 14, 2020; (10 pages).
Anonymous; "Floseal Instructions for Use"; Floseal Hemostatic Matrix; Apr. 6, 2015; http://www.floseal.com/int/pdf/FLOSEAL_IFU_EU.pdf.
Notice of Reasons for Refusal for Japanese Patent Application No. 2021-520571 dated Oct. 28, 2022.
Notification of First Office Action and English Translation from corresponding Chinese Patent Application No. 201880098795.0, dated Jan. 25, 2024. 17 pages.
Baxter Healthcare SA. (2015). Floseal Hemostatic Matrix 5ml/10ml: Instructions for Use (English). Zurich, Switzerland: Author. pp. 1-7.
Singaporean Written Opinion from corresponding Singaporean Patent Application No. 11202102248P, mailed Nov. 15, 2022.
Indian Examination Report from corresponding Indian Patent Application No. 202117017385, mailed Jan. 10, 2023.
International Preliminary Report on Patentability for related International Application No. PCT/US2018/059628; action dated May 20, 2021; (12 pages).
European Office Action from corresponding European Patent Application No. 18807525.3, mailed Sep. 6, 2023. 4 pages.
Korean Office Action from corresponding Korean Patent Application No. 10-2021-7016697, mailed Sep. 6, 2023. 6 pages.
Indian Examination Report from corresponding Indian Patent Application No. 202117017385, mailed Oct. 1, 2023. 5 pages.
Second Chinese Office Action for corresponding Chinese Patent Application No. 201880098795.0, dated Jul. 19, 2024. 6 pages.
Chinese Decision of Rejection from corresponding Chinese Patent Application No. 201880098795.0, dated Nov. 8, 2024. 19 pages.

* cited by examiner

FIG. 7B ial Application No. PCT/US2018/059628, filed on Nov. 7, 2018, the contents of which are all hereby incorporated by reference herein in their entirety.
DUAL CHECK VALVE ONE HANDED APPLICATOR

CROSS-REFERENCE TO RELATED APPLICATIONS

The present application is a National Stage of International Application No. PCT/US2018/059628, filed on Nov. 7, 2018, the contents of which are all hereby incorporated by reference herein in their entirety.

BACKGROUND

In medical applications, it is important to prevent excessive bleeding. Numerous procedures and related materials currently exist to prevent excessive bleeding and thus reduce transfusion rates and other minor complications during surgery. One such example involves introducing barrier materials such as metals, polymers, and natural materials onto a bleeding site. These products, however, may not conform well to the underlying tissue. Other materials, such as nylon, cellophane, polytetrafluoroethylene, polyethylene, siloxane, elastomers, and polylactic acid copolymer films, are more flexible but not biodegradable and, therefore, remain in the body with unpredictable and potentially undesirable consequences. Additionally, placement and immobilization of implants onto the bleeding site is often challenging.

Alternate materials for preventing excessive bleeding may include non-solid anti-adhesive materials, such as hemostatic matrix materials. Use of these materials requires that they be sufficiently fluid to enter and conform to the regions being treated, while simultaneously being sufficiently viscous to remain on the bleeding site until the tissue is healed. Viscous materials often require higher pressure forces for delivery. For example, it is often difficult to manually extrude a viscous material through a syringe. Furthermore, delivery of non-solid anti-adhesive materials to the bleeding site, on or in the body, necessitates a high degree of user-control. Materials should be delivered in a controlled fashion, so as to target the site of therapeutic effect, such as the bleeding site. For at least these reasons, any purported delivery device must be easy to use and control.

Typical procedures for delivery of a hemostatic material may include loading a delivery tube with hemostatic material. Specifically, a surgeon may load the delivery tube by filling it up via a syringe. This can be a time intensive process. Typically, in such a process, the delivery tube is positioned, by the surgeon, at a location on the patient's body. The surgeon then inserts a stylet, which is concentric with the delivery tube, into the back-end of the delivery tube. By inserting the stylet into the back-end of the delivery tube, hemostatic material is expelled from the front-end of the delivery tube at the location on the patient's body. This procedure requires two-hand implementation: one hand for holding and positioning the delivery tube and one hand for pushing the stylet. It is preferable to implement one-handed procedures. Moreover, because the stylet may not translate all the way through the delivery tube, a portion of hemostatic material may remain in the delivery tube, thus wasting hemostatic material. It is preferable to avoid needless wasting of hemostatic material.

For the above reasons, it is desirable to provide improved delivery devices, delivery systems, and related methods, for precise administration of hemostatic compositions.

SUMMARY

To improve medical treatment, especially to prevent excessive bleeding, new delivery devices, delivery systems, and methods of delivery are described herein. The present disclosure seeks to implement new devices, systems, and methods for delivering compositions to the patient with a high degree of user control, regarding both the delivery location and the delivery rate, which may additionally reduce clogging of the delivery device, improve preparation time associated with readying the delivery device for use, and reduce wasted material associated with incomplete delivery.

In light of the disclosure herein, and without limiting the scope of the invention in any way, in a first aspect of the present disclosure, which may be combined with any other aspect listed herein unless specified otherwise, a delivery device includes a trigger mechanism, a pusher, a valve, and a cannula. The pusher is configured to engage with the trigger mechanism and retain a first syringe at least by coupling with a plunger of the first syringe. The valve is fluidly coupled to the first syringe. The cannula extends distally from and is fluidly coupled to the valve. Activation of the trigger mechanism causes the pusher and the plunger of the first syringe to translate in a distal direction, such that a composition in the first syringe is expelled out of the first syringe, through the valve, through the cannula, and out of a distal end of the cannula. The valve is further configured to engage with a second syringe, such that the second syringe is in fluid communication with both the valve and the first syringe.

In a second aspect of the present disclosure, which may be combined with any other aspect listed herein unless specified otherwise, prior to activation of the trigger mechanism, the composition is expelled out of the second syringe, through the valve, and into the first syringe, such that the first syringe is filled with the composition via the second syringe.

In a third aspect of the present disclosure, which may be combined with any other aspect listed herein unless specified otherwise, engagement between the valve and the second syringe is a luer lock engagement.

In a fourth aspect of the present disclosure, which may be combined with any other aspect listed herein unless specified otherwise, the valve is a two-way check valve.

In a fifth aspect of the present disclosure, which may be combined with any other aspect listed herein unless specified otherwise, the valve is a user-selectable stopcock valve.

In a sixth aspect of the present disclosure, which may be combined with any other aspect listed herein unless specified otherwise, the pusher includes a plurality of teeth, and wherein the trigger mechanism includes a ratchet, the ratchet configured to engage with the plurality of teeth of the pusher.

In a seventh aspect of the present disclosure, which may be combined with any other aspect listed herein unless specified otherwise, the composition is a viscous hemostatic material.

In a eighth aspect of the present disclosure, which may be combined with any other aspect listed herein unless specified otherwise, the device further includes a window indicator that indicates an amount of the composition remaining in the first syringe.

In a ninth aspect of the present disclosure, which may be combined with any other aspect listed herein unless specified otherwise, the cannula includes an inner cannula configured to deliver the composition and an outer cannula, the outer cannula disposed concentrically around the inner cannula.

In a tenth aspect of the present disclosure, which may be combined with any other aspect listed herein unless specified otherwise, the outer cannula is stainless steel.

In a eleventh aspect of the present disclosure, which may be combined with any other aspect listed herein unless specified otherwise, a delivery system includes a delivery device. The delivery device includes a trigger mechanism, a pusher, a valve, and a cannula. The pusher is configured to engage with the trigger mechanism and retain a first syringe at least by coupling with a plunger of the first syringe. The valve is fluidly coupled to the first syringe. The cannula extends distally from and is fluidly coupled to the valve. The delivery system further includes a second syringe fluidly coupled to the valve, the second syringe further including a composition. Depressing a plunger of the second syringe causes the composition to be expelled out of the second syringe, through the valve, and into the first syringe. Activation of the trigger mechanism causes the pusher and the plunger of the first syringe to translate in a distal direction, such that the composition in the first syringe is expelled out of the first syringe, through the valve, through the cannula, and out of a distal end of the cannula.

In a twelfth aspect of the present disclosure, which may be combined with any other aspect listed herein unless specified otherwise, the valve is a two-way check valve, such that the composition can only flow in a first direction, from the second syringe through the valve into the first syringe, and in a second direction, from the first syringe through the valve into the cannula.

In a thirteenth aspect of the present disclosure, which may be combined with any other aspect listed herein unless specified otherwise, engagement between the valve and the second syringe is a luer lock engagement.

In a fourteenth aspect of the present disclosure, which may be combined with any other aspect listed herein unless specified otherwise, the composition is a viscous hemostatic material.

In a fifteenth aspect of the present disclosure, which may be combined with any other aspect listed herein unless specified otherwise, the cannula includes an inner cannula configured to deliver the composition and an outer cannula, the outer cannula disposed concentrically around the inner cannula.

In a sixteenth aspect of the present disclosure, which may be combined with any other aspect listed herein unless specified otherwise, a method of delivering a composition includes attaching a supply syringe to a valve of a delivery device, the supply syringe including the composition. The method includes depressing a plunger of the supply syringe such that, responsive to depressing the plunger, the composition is expelled out of the supply syringe, through the valve, and into a delivery syringe. The method includes activating a trigger mechanism of the delivery device such that, responsive to activating the trigger mechanism, a plunger of the delivery syringe is depressed and the composition is expelled out of the delivery syringe, through the valve, and into a cannula. The method includes further depressing the plunger of the supply syringe such that, responsive to depressing the plunger, additional composition is expelled out of the supply syringe, through the valve, and into the delivery syringe. The method includes further activating the trigger mechanism of the delivery device such that, responsive to activating the trigger mechanism, the plunger of the delivery syringe is depressed and the additional composition is expelled out of the delivery syringe, through the valve, and into the cannula.

In a seventeenth aspect of the present disclosure, which may be combined with any other aspect listed herein unless specified otherwise, the method includes detaching the supply syringe from the valve of the delivery device. The method includes attaching a flush syringe to the valve of the delivery device, the flush syringe including a flushing fluid different from the composition. The method includes depressing a plunger of the flush syringe such that, responsive to depressing the plunger, the flushing fluid is expelled out of the flush syringe, through the valve, and into the delivery syringe. The method includes activating the trigger mechanism of the delivery device such that, responsive to activating the trigger mechanism, the plunger of the delivery syringe is depressed and the flushing fluid is expelled out of the delivery syringe, through the valve, and into the cannula, such that the flushing fluid pushes the composition out of the cannula.

In a eighteenth aspect of the present disclosure, which may be combined with any other aspect listed herein unless specified otherwise, the flushing fluid is saline, or other liquid medium, or gas.

In a nineteenth aspect of the present disclosure, which may be combined with any other aspect listed herein unless specified otherwise, prior to initially attaching the supply syringe to the valve of the delivery device, the composition is prepared for administration in the supply syringe.

In a twentieth aspect of the present disclosure, which may be combined with any other aspect listed herein unless specified otherwise, a kit includes a pre-filled sodium chloride solution syringe, a thrombin vial, a pre-filled gelatin matrix syringe, and a delivery device. The delivery device includes a trigger mechanism, a pusher, a valve, and a cannula. The pusher is configured to engage with the trigger mechanism, the pusher further configured to retain a delivery syringe at least by coupling with a plunger of the delivery syringe. The valve is fluidly coupled to the delivery syringe. The cannula extends distally from and is fluidly coupled to the valve. The pre-filled gelatin matrix syringe fluidly couples to the valve. Depressing a plunger of the pre-filled gelatin matrix syringe causes a composition is expelled out of the pre-filled gelatin matrix syringe, through the valve, and into the delivery syringe. Activation of the trigger mechanism causes the pusher and the plunger of the delivery syringe to translate in a distal direction, such that the composition in the delivery syringe is expelled out of the delivery syringe, through the valve, through the cannula, and out of a distal end of the cannula.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

Understanding that the figures depict only typical embodiments of the invention and are not to be considered to be limiting the scope of the present disclosure, the present disclosure is described and explained with additional specificity and detail through the use of the accompanying figures. The figures are listed below.

DETAILED DESCRIPTION OF EXAMPLE EMBODIMENTS

As discussed briefly above, this disclosure is, in various embodiments, directed to devices, systems, and methods for inhibiting bleeding by applying a material topically to a wound site. The material is typically a hemostatic matrix material, such as a flowable hemostatic material. In particular embodiments, the delivery devices, systems, and methods are configured to deliver a viscous hemostatic matrix, such as FLOSEAL® VH S/D (also known as FLOSEAL® HEMOSTATIC MATRIX VH S/D, FLOSEAL® HEMOSTATIC MATRIX, and FLOSEAL®) (Baxter Healthcare Corporation), a bovine-derived gelatin matrix combined with a human-derived thrombin solution. It should be appreciated, however, that the delivery devices, systems, and methods disclosed herein may deliver other materials, such as any viscous materials, liquid materials, solid materials, or gaseous materials.

Prior to applying a hemostatic material, the bleeding tissue is generally blotted or gently suctioned to remove excess blood so that the hemostatic material can be applied immediately and directly to the site of active bleeding. Minimizing contact of the syringe or applicator tip with wet surfaces may reduce clogging of the syringe and/or the applicator tip. Similarly, clogging can be prevented by particular configurations of the delivery device or delivery system as discussed herein. After the hemostatic material is applied, gentle approximation is typically applied over the treated site using a non-adhering substrate such as moistened gauze. After an initial application, a user may apply additional hemostatic material if bleeding persists. If the non-adhering substrate adheres to the wound site, gentle irrigation with non-heparinized saline may aid in removal of the substrate with minimal disruption to the clot. Once bleeding has ceased, hemostatic material not incorporated into the clot is carefully removed by gentle irrigation and suctioned away from the treatment site.

Delivery of the compositions of the present disclosure is particularly suitable to inhibit bleeding (causing hemostasis) on an abraded or damaged tissue surface, which could be any organ surface such as the liver, spleen, heart, kidney, intestine, blood vessels, other vascular organs, and the like. For example, a delivery device or delivery system described herein may be used to apply the hemostatic material to the active bleeding area. Exemplary methods for applying the material include dispensing the material directly from the delivery device or using an applicator tip. An endoscopic applicator may be used to deliver the hemostatic material to the site of bleeding, as it is often difficult to access the site within the patient's body cavity.

As previously noted, typical endoscopic applicators cannot be easily used with one hand. For example, a typical applicator implements a hollow tube loaded with hemostatic material and a stylet that is manually inserted into the hollow tube to dispense the hemostatic material. This arrangement leaves room for improvement for several reasons. First, loading the endoscopic applicator requires the user to manually load the hollow tube by filling it (via a source syringe), which is often a time intensive process. Second, the source syringe needs to be disconnected from the hollow tube, so that the stylet can be inserted into the hollow tube for delivery. Third, positioning the endoscopic applicator requires the user to awkwardly hold the hollow tube with one hand, positioning the distal end at the delivery site, while simultaneously holding the stylet with the other hand. Fourth, delivery of material via the endoscopic applicator requires the user to simultaneously push the stylet into the hollow tube with one hand, while keeping the other hand still to ensure precise delivery. This is all the more difficult with viscous materials that require higher pressure forces for extrusion. Fifth, it is difficult for the user to gauge the quantity of delivered hemostatic material or rate of delivery. Finally, though not exhaustively, even when expelled to the full capability of the device, a holdup volume of hemostatic material remains unused in the hollow tube and on the stylet surface, effectively becoming waste material.

In comparison to the typical applicator system described above, the delivery devices, delivery systems, and related methods disclosed herein advantageously provide for precise administration, a high degree of user control regarding delivery location and delivery rate, reduced clogging, improved preparation time, and reduced wasted material.

Delivery Device and Delivery System

Figure 1:
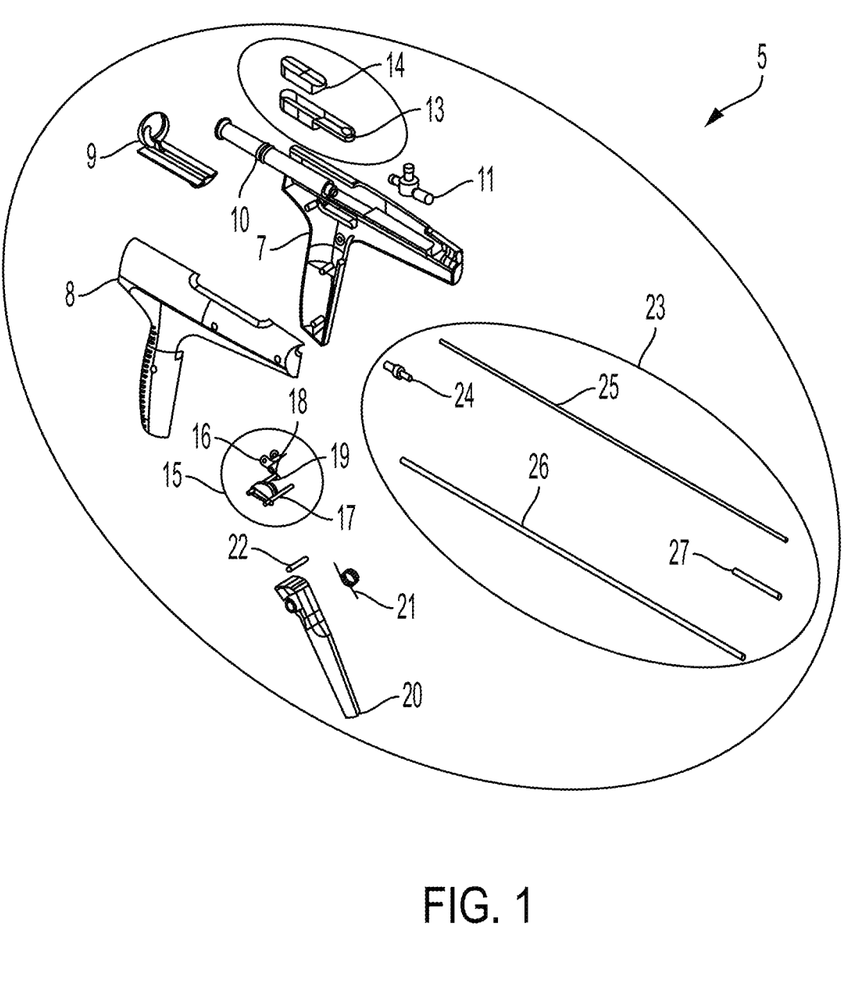
FIG. 1 is an exploded perspective view of a delivery device, according to an example embodiment of the present disclosure.

Referring now to FIG. 1, an exploded perspective view of a delivery device 5 is illustrated. In an embodiment, delivery device 5 includes a two-piece molded housing, including a left housing 7 and a right housing 8. Each of the left housing 7 and right housing 8 are configured to couple to one another. In various embodiments, coupling can be accomplished via frictional fitting, mechanical press-fit, ultrasonic welding, or any other mechanical engagement. In an embodiment, left housing 7 and right housing 8 are constructed of injection-molded polycarbonate, glass-filled polyamide polymer, or other related material. Alternatively, the assembly of the left housing 7 and right housing 8, also referred to herein as the "entire housing," may be injection molded as one piece of material, such as polypropylene, PVC, non-DEHP PVC, polyethylene, polystyrene, polypropylene mixture, or other similar materials and/or formed via other means such as 3D printing or other similar plastics manufacturing methods. In an embodiment, the entire housing is configured to be handheld, such that a user can hold the delivery device 5 in one hand.

Delivery device 5 includes a pusher 9, which may be constructed of injection-molded polycarbonate, glass-filled polyamide polymer, or other related material. Delivery device 5 further includes a reservoir syringe 10, having a plunger, assembled and arranged to engage and seal with an inner cylindrical surface of a barrel of the reservoir syringe 10. In this way, the plunger may translate along a length of the barrel of the reservoir syringe 10. Each of the plunger and barrel of the reservoir syringe 10 may be constructed of any suitable plastic material, such as polypropylene, PVC, non-DEHP PVC, polyethylene, polystyrene, polypropylene mixture, or other similar materials. Preferably, each of the plunger and barrel of the reservoir syringe 10 are constructed of polypropylene, but it should be appreciated that any known material or combination of materials could be employed for this function. In an embodiment, the reservoir syringe 10 contains a composition, such as a viscous hemostatic material.

Pusher 9 is configured to actuate the barrel of the reservoir syringe 10. Specifically, the pusher 9 is configured to retain the reservoir syringe 10, at least by coupling with the plunger of the reservoir syringe 10. In an embodiment, the pusher 9 includes a slot configured to receive a flanged end of the plunger of reservoir syringe 10. When pusher 9 translates, the barrel of the reservoir syringe 10 likewise translates. Translation of pusher 9 thus actuates reservoir syringe 10.

Delivery device 5 includes a trigger mechanism 15 that, when activated, causes pusher 9 to translate. In one embodiment, trigger mechanism 15 includes an engagement pawl 16, an engagement rack 17, an engagement spring 18, an engagement pin 19, a trigger 20, a trigger spring 21, and a trigger pin 22. It should be appreciated that each of engagement pawl 16, engagement rack 17, and trigger 20 may be constructed of injection-molded polycarbonate, glass-filled polyamide polymer, or other related material. Likewise, it should be appreciated that each of the springs and pins may be constructed of metal, such as 302 stainless steel, or other related metals.

Figure 2:
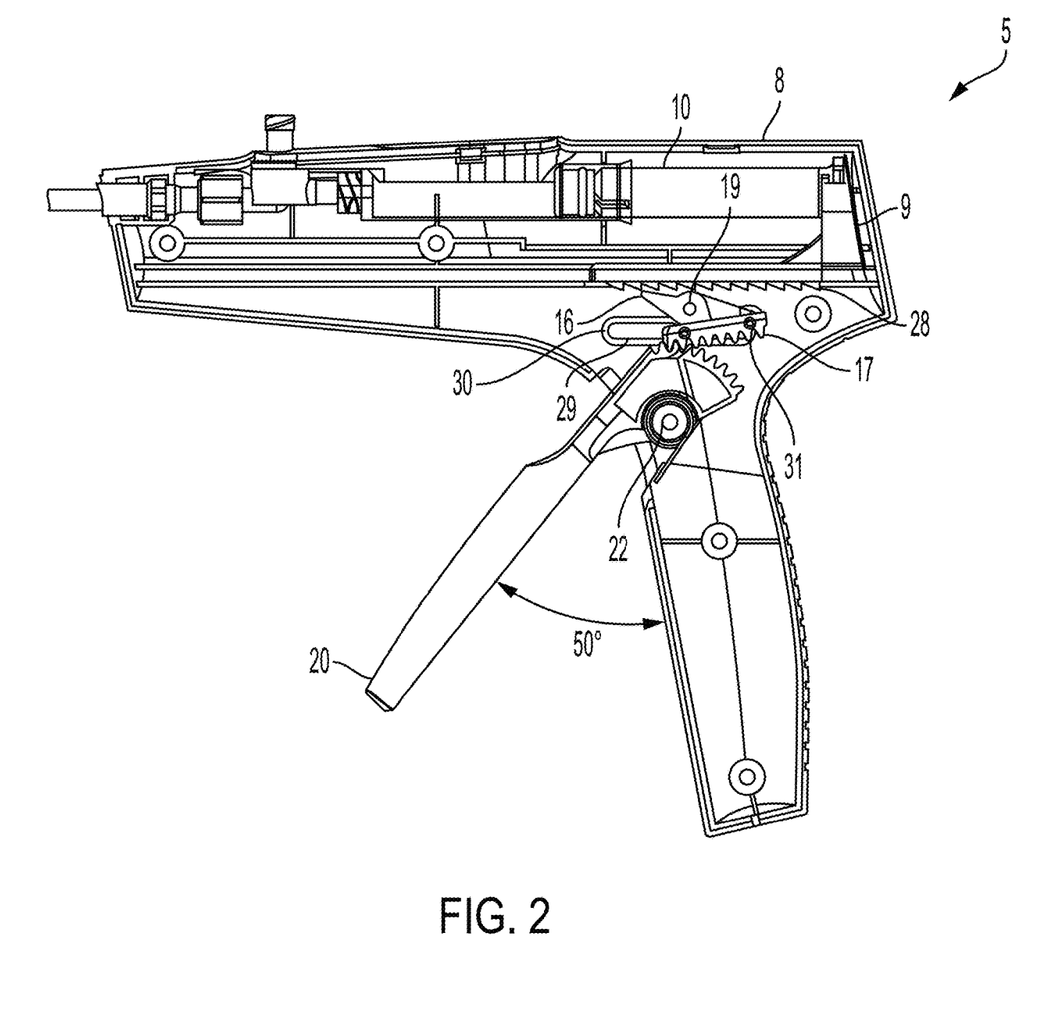
FIG. 2 is an exploded side elevation view of a delivery device in a first trigger configuration, according to an example embodiment of the present disclosure.
Figure 3:
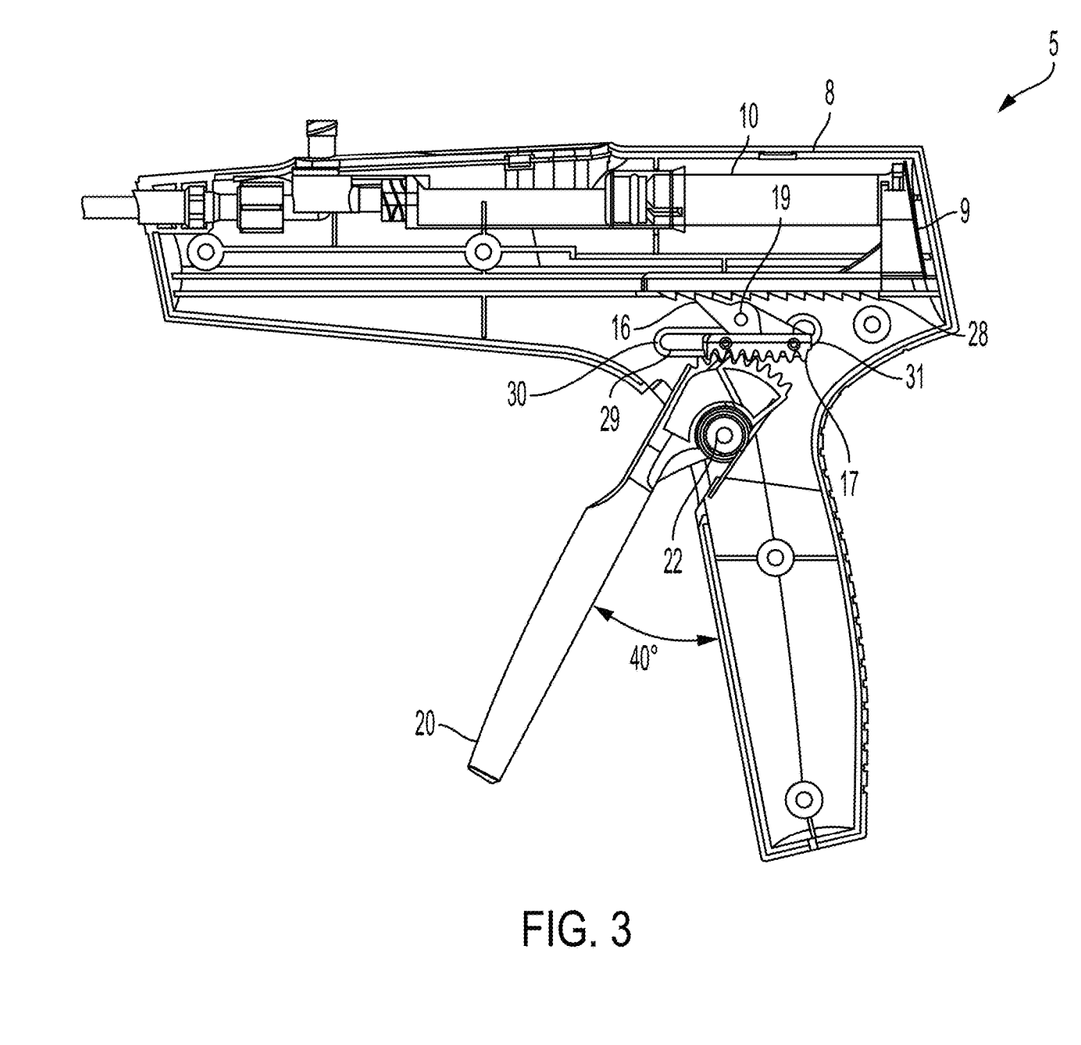
FIG. 3 is an exploded side elevation view of a delivery device in a second trigger configuration, according to an example embodiment of the present disclosure.
Figure 4:
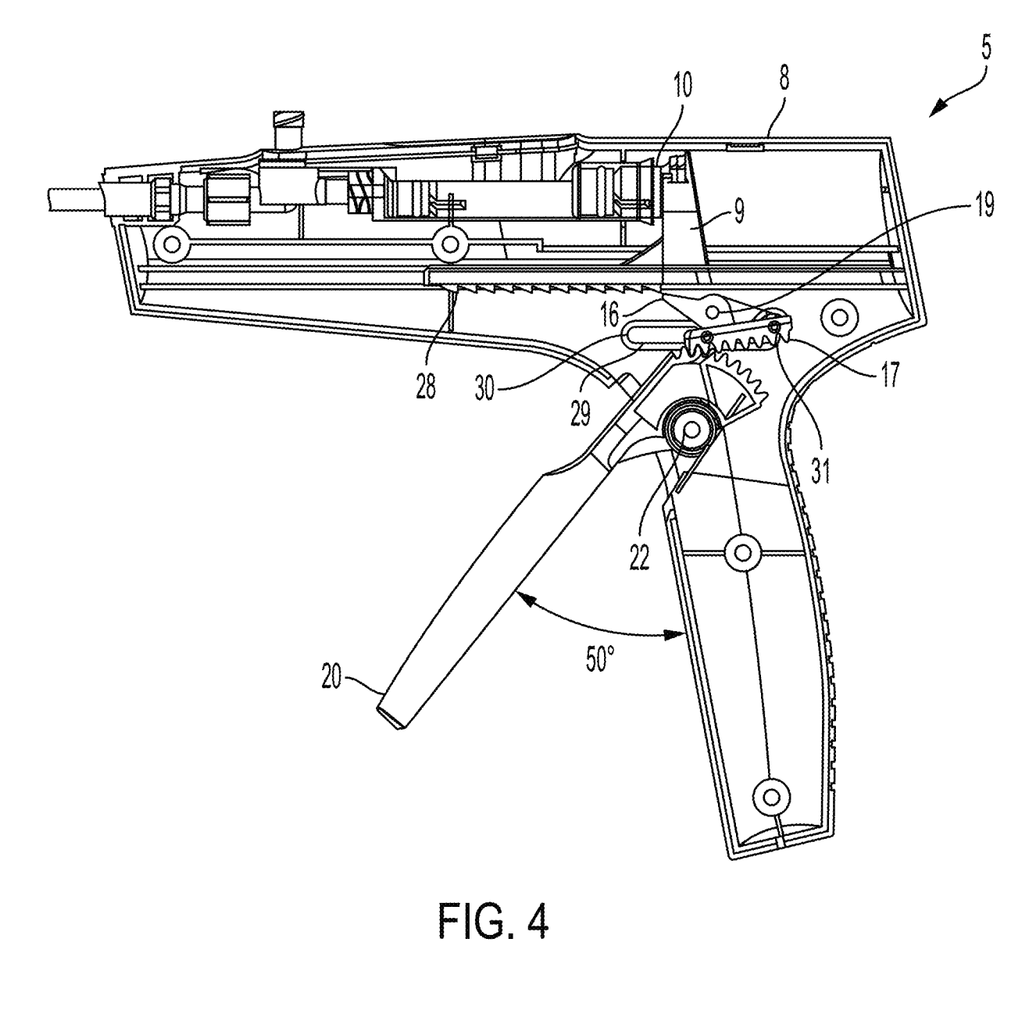
FIG. 4 is an exploded side elevation view of a delivery device in a third trigger configuration, according to an example embodiment of the present disclosure.

Referring now to FIGS. 2 to 4, an exploded side view of a delivery device 5 is illustrated in various trigger configurations. More particularly, FIGS. 2 to 4 illustrate how pusher 9 engages with trigger mechanism 15, and its subcomponents. In this way, rotational force, such as that imparted by the user onto trigger 20 of trigger mechanism 15, is converted into linear force that translates pusher 9 for syringe actuation.

More specifically, the bottom of pusher 9 may include pusher teeth 28, or some other type of ridges such as linear gear teeth, which interface with engagement pawl 16. Engagement pawl 16 may be spring-loaded, with engagement spring 18 (not illustrated) and pivotable about engagement pin 19, such that engagement pawl 16 is biased in a particular direction toward pusher 9 and pusher teeth 28. Generally, engagement pawl 16, engagement rack 17, engagement spring 18, and engagement pin 19 are coupled to one another and may commonly be referred to as a mechanical dog that engages with the pusher teeth 28 of pusher 9. Because engagement pawl 16 is biased in a particular direction toward pusher 9, such as an angled direction, pusher 9 translates with engagement rack 17 and engagement pawl 16 in a particular direction, such as a distal direction toward cannula 23; pusher 9 does not translate with engagement rack 17 and engagement pawl 16, when those components translate in an opposite direction. For example, when engagement rack 17 and engagement pawl 16 translate in a proximal direction away from cannula 23, pusher 9 does not translate; rather, pusher 9 remains in its current position. In this way, delivery device 5 implements a ratchet effect, described in greater detail below.

Engagement rack 17 further engages with the top of trigger 20. For example, each of engagement rack 17 and the top of trigger 20 may include teeth or ridges, such as linear or curved gear teeth, so that force can be translated from trigger 20 to engagement rack 17. Trigger 20 is pivotable about trigger pin 22, and biased in an open configuration by trigger spring 21 (not illustrated).

Further, delivery device 5 includes a slot 29 with a straight end 30 and a curved end 31. In an embodiment, slot 29 is located on one of the left housing 7 or the right housing 8. In a different embodiment, slot 29 is located on both of the left housing 7 and the right housing 8. Engagement rack 17 and its related components interface with the slot 29, such that the slot 29 restricts motion of the engagement rack 17 to directions defined by the slot 29, including straight directions and curved directions. Because the slot 29 includes both a straight end 30 and a curved end 31, the slot 29 provides engagement and disengagement of engagement pawl 16 from the pusher teeth 28.

For example, FIG. 2 illustrates a first trigger configuration, where the trigger 20 extends approximately fifty degrees from a handle of delivery device 5. Each of engagement rack 17 and the top of trigger 20 include teeth, which engage one another. Because trigger 20 is located in an open position, such as at fifty degrees from the handle, the teeth on the trigger 20 push the engagement rack 17 in a proximal direction along slot 29. Specifically, engagement rack 17 is located at the curved end 31 of slot 29. Because a portion of engagement rack 17 is at the curved end 31, the engagement rack 17 pivots slightly from the direction defined by the straight end 30 of slot 29. In this way, pivoting the engagement rack 17 disengages the engagement pawl 16 from the pusher teeth 28. Disengagement is useful, for example, so that the user can manually translate pusher 9 in the proximal direction to load the reservoir syringe 10 into the delivery device 5, or so that the user can fill or re-fill the reservoir syringe 10, as described in greater detail below.

It should be appreciated that the engagement pawl 16 is disengaged when trigger 20 is fifty degrees from the handle of delivery device 5; however, alternate disengagement configurations of trigger 20 are contemplated and the engagement pawl 16 may be disengaged at any other rotational orientation of trigger 20. Furthermore, the specific configuration and geometry of engagement pawl 16, engagement rack 17, and the slot 29 including the straight end 30 and the curved end 31 may affect the extent of disengagement.

FIG. 3 illustrates a second configuration, where the trigger 20 extends approximately forty degrees from the handle of delivery device 5. For example, in this second configuration the user has partially squeezed trigger 20. As a reminder, each of engagement rack 17 and the top of trigger 20 include teeth, which engage one another. Because trigger 20 is partially squeezed, the teeth on the trigger 20 rotate and push the engagement rack 17 in a distal direction along slot 29. Engagement rack 17 is no longer located at the curved end 31 of slot 29, and it therefore does not pivot away from the direction defined by the straight end 30 of slot 29. By not pivoting, engagement rack 17 directly engages the engagement pawl 16 with the pusher teeth 28. Engagement is useful, for example, so that the user can deliver material from reservoir syringe 10 by squeezing trigger 20.

More specifically, when the user squeezes trigger 20, trigger 20 rotates about trigger pin 22 to a closed configuration. As trigger 20 is squeezed, the rotational motion of trigger 20 converts into a linear motion at engagement rack 17, via engagement between the gear teeth of these components. Thus, engagement rack 17 and its related components translate in a linear direction. For example, these components translate along the slot 29 towards the straight end 30.

The linear motion of engagement rack 17 and engagement pawl 16 is further converted to linear motion of pusher 9, via engagement between the engagement pawl 16 and the pusher teeth 28 as discussed above. In other words, as engagement rack 17 and engagement pawl 16 translate towards the straight end 30 of slot 29, pusher 9 translates toward the distal end of delivery device 5. In this way, trigger mechanism 15 effectively converts rotational motion from trigger 20 into linear motion at pusher 9. Also, as noted previously, because pusher 9 retains the reservoir syringe 10, translation of pusher 9 actuates reservoir syringe 10.

When the user releases trigger 20, trigger spring 21 biases trigger 20 to rotate about trigger pin 22 toward the open position. As trigger 20 is released, the rotational motion of trigger 20 converts into a linear motion at engagement rack 17, via engagement between the gear teeth of these components. Each of the engagement rack 17 and its related components translate linearly, along the slot 29 towards the curved end 31.

However, as engagement rack 17 and engagement pawl 16 translate along the slot 29 towards the curved end 31, pusher 9 does not translate. For example, as previously noted, the engagement between engagement pawl 16 and pusher teeth 28 may commonly be referred to as a mechanical dog. Engagement pawl 16 is biased in a particular angled direction toward pusher 9, such that pusher 9 only translates with engagement rack 17 and engagement pawl 16 in a particular direction, such as the distal direction toward cannula 23; pusher 9 does not translate with engagement rack 17 and engagement pawl 16 when those components translate in the opposite direction. Due to this configuration, the user may repeatedly squeeze and release trigger 20. The entire trigger mechanism 15 has a ratchet effect for engaging pusher 9, to repeatedly translate pusher 9 in the distal direction and repeatedly actuate reservoir syringe 10.

Once delivery device 5 has completely delivered the material in reservoir syringe 10, pusher 9 will have translated to its distal-most point. At this configuration, it is advantageous for the user to have the ability to disengage engagement rack 17 and engagement pawl 16, such as to load a new reservoir syringe 10.

FIG. 4 illustrates a third trigger configuration, where the trigger 20 extends approximately fifty degrees from the handle of delivery device 5. Similar to FIG. 2, because trigger 20 is located in the open position, such as at fifty degrees, engagement rack 17 is located at the curved end 31 of slot 29, thus pivoting slightly from the direction defined by the straight end 30 of slot 29. In this way, engagement rack 17 disengages the engagement pawl 16 from the pusher teeth 28. Disengagement is useful, for example, so that the user can manually slide pusher 9 in the proximal direction to load a new reservoir syringe 10 into the delivery device 5, or so that the user can fill or re-fill the reservoir syringe 10, as described in greater detail below. It should be appreciated that trigger 20 may include alternate disengagement configurations.

Additionally, the disengagement of engagement rack 17 and engagement pawl 16 is beneficial for other reasons, beyond reservoir syringe 10 loading, replacement, and/or filling and re-filling. Specifically, disengagement of engagement rack 17 and engagement pawl 16 advantageously creates a pressure-release between successive squeezes of trigger 20. As the user is repeatedly squeezing trigger 20, the pusher 9 translates in the distal direction and pressure within the reservoir syringe 10 is increasing. This pressure is largely relieved as material exits the delivery device 5 via cannula 23. However, due to the viscosity of certain materials in reservoir syringe 10, a pressure differential can remain within reservoir syringe 10, causing undesirable leakage from reservoir syringe 10. To alleviate this pressure differential, delivery device is configured for pressure release. For example, the user may squeeze trigger 20, such as from fifty degrees to forty degrees, to expel material from the reservoir syringe. When the user releases trigger 20, trigger 20 is biased back to its open configuration of fifty degrees. In this open configuration, engagement rack 17 and engagement pawl 16 are disengaged from pusher teeth 28. Thus, pusher 9 is free to translate slightly in a distal direction, to relieve any pressure differential remaining within reservoir syringe 10.

Furthermore, it should be appreciated that pusher 9 may engage with trigger mechanism 15 by any other related mechanical means and components, such as additional gears, pawls, and springs; these other mechanical components may be used to translate motion from the trigger mechanism 15 to the pusher 9. Thus, regardless of the particular configuration, as the trigger mechanism 15 is actuated, the trigger mechanism 15 will translate motion to the pusher 9.

Referring again to FIG. 1, the delivery device further includes a window housing 13 including clear window 14 so that the user can see the reservoir syringe 10. The clear window 14 may further include gradients or physical markings that the user may associate with a volume of composition remaining in reservoir syringe 10 and/or a volume of composition expressed from reservoir syringe 10.

Delivery device 5 further includes a valve 11 configured to fluidly couple to the reservoir syringe 10. In an embodiment, valve 11 is further configured to fluidly couple to a second syringe, as described in greater detail herein.

Delivery device 5 includes a cannula 23, configured to deliver the composition to the delivery site. Cannula 23 is configured to engage with the valve 11 at connection point 24, so that cannula 23 is in fluid communication with valve 11. In an embodiment, connection point 24 is a luer lock fitting. In alternate embodiments, engagement between valve 11 and connection point 24 of cannula 23 may be threaded engagement, interference-fit engagement, hook-and-loop engagement, snap engagement, magnetic engagement, or any other sort of mechanical engagement for affixing the cannula 23 to the valve 11. In a preferred embodiment, cannula 23 is a single lumen cannula. Cannula 23 may be provided in any variety of lengths, such as between 10 and 46 cm to support a number of different surgical applications including pediatric surgery and spinal surgery. In an embodiment, cannula 23 is trimmable, such that the user can customize the length of cannula 23 to particular surgical applications. Cannula 23 extends in the distal direction and includes a tip 27 at its distal end. In various embodiments, the tip 27 may be a rigid extension tip, a trimmable extension tip, a flexible tip, or a malleable tip such as a polyurethane tip with a stainless steel wire for manipulation by the user.

In an alternate embodiment, cannula 23 may include multiple lumens, such as an inner cannula 25, an outer cannula 26, and the tip 27. The inner cannula 25 may be configured to deliver the composition to the delivery site. Inner cannula 25 may preferably have an inner diameter of 1 to 5 mm, which may optimize residual volume of the composition that remains inside inner cannula 25 after delivery. The diameter of inner cannula 25 may also be optimized for the particular material delivered from reservoir syringe 10; for example, the diameter of the inner cannula 25 may be determined with respect to the viscosity of the material, such as to avoid clogging of inner cannula 25. Likewise, for example, the outer cannula 26 may be configured to be disposed concentrically around the inner cannula 25, to protect inner cannula 25. In an example, outer cannula 26 is constructed of stainless steel. Outer cannula 26 may preferably have a 41 cm length to support all surgical specialties, including endoscopic applications. Outer cannula 26 additionally provides enhanced rigidity to the entire cannula 23, which is beneficial during surgical maneuvering and manipulation.

As previously noted, reservoir syringe 10 may contain the composition. Responsive to engagement of the trigger mechanism 15, the pusher 9 and the plunger of the reservoir syringe 10 translate in the distal direction, toward the tip 27 of cannula 23. In this way, the composition in the reservoir syringe 10 is expelled out of the reservoir syringe 10, through the valve 11, through the cannula 23 (or alternatively through the inner cannula 25 of cannula 23), and out of tip 27 at the distal end of the cannula 23.

Figure 5A:
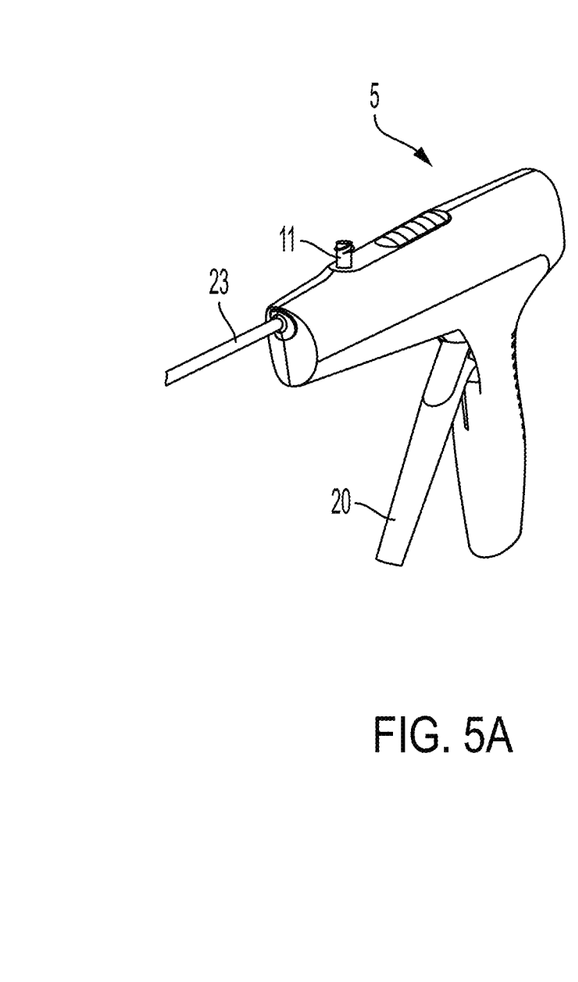
FIGS. 5A to 5B are perspective views of a delivery device, according to an example embodiment of the present disclosure.
Figure 5B:
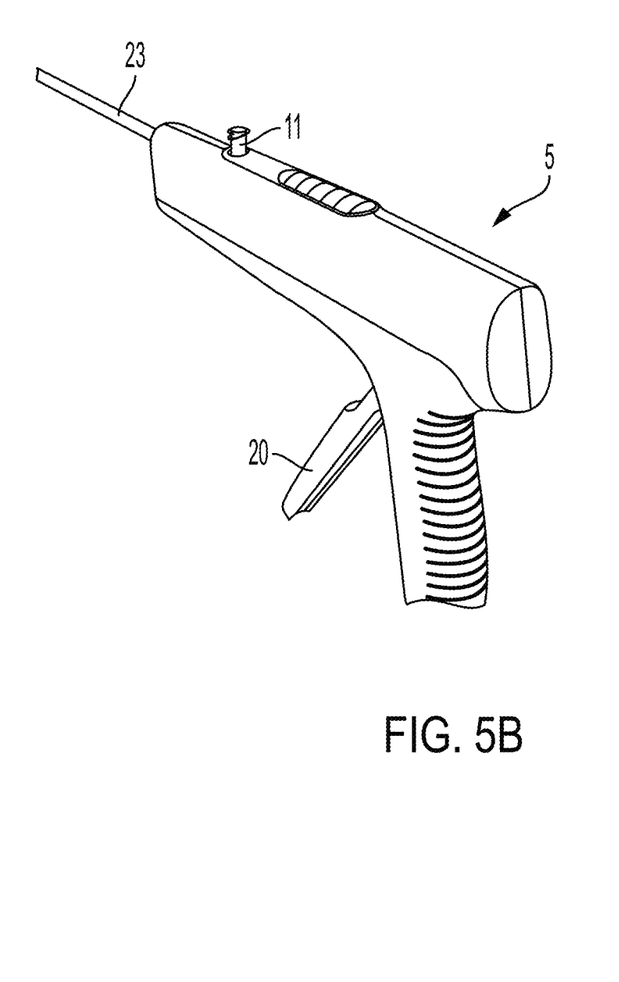

FIGS. 5A to 5B illustrate perspective views of delivery device 5. As illustrated, delivery device 5 includes valve 11, trigger 20, and cannula 23. It should be appreciated that delivery device 5 is self-contained, and thus may include all other aspects as described in greater detail above, such as the remaining components of trigger mechanism 15 and reservoir syringe 10. Preferably, delivery device 5 is dimensioned and ergonomically designed for one-handed use by the user.

Figure 6:
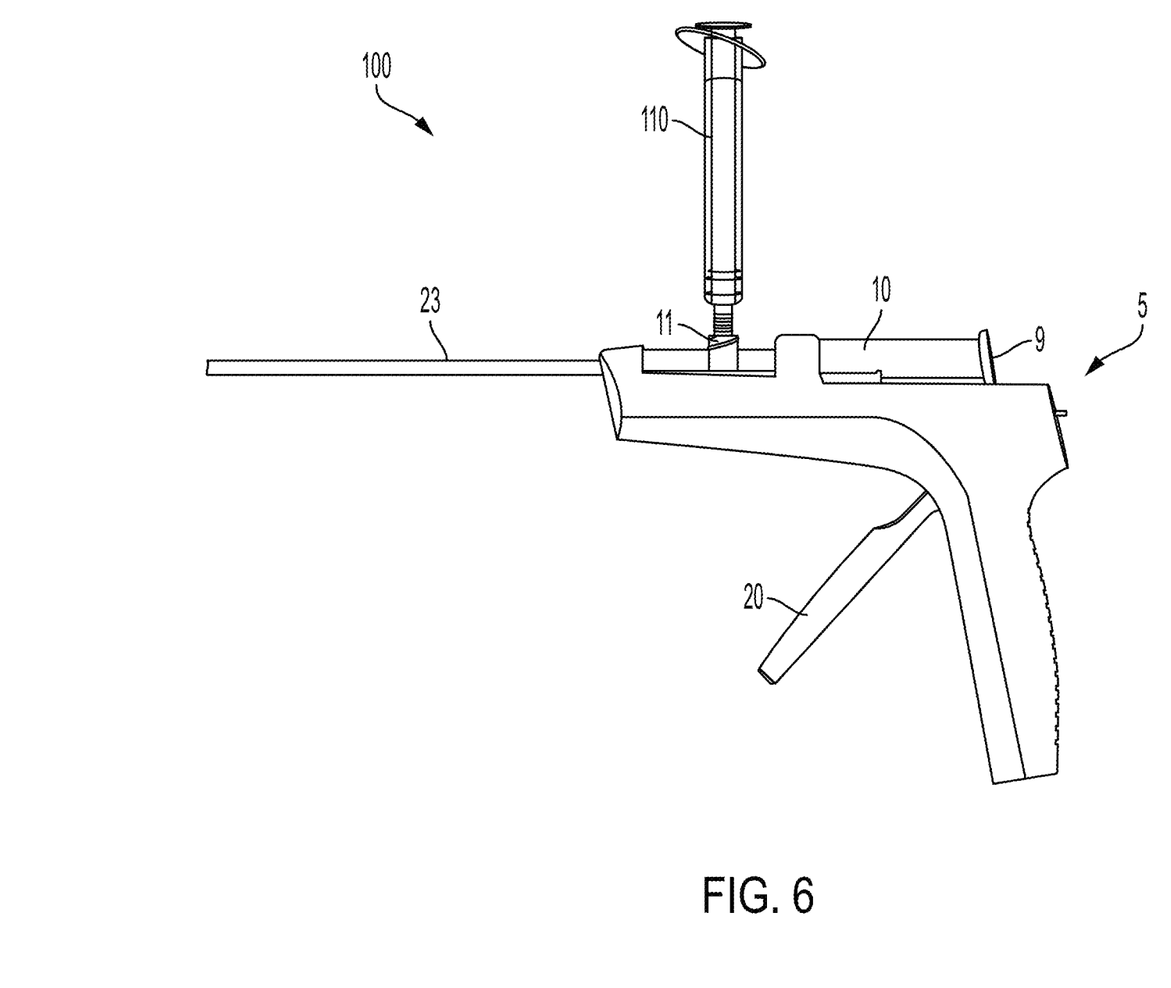
FIG. 6 is a side elevation view of a delivery system, according to an example embodiment of the present disclosure.

Valve 11 is further configured to engage with a second syringe, such as a supply syringe. For example, FIG. 6 illustrates a side elevation view of a delivery system 100, which includes a supply syringe 110. Initially, it should be appreciated that portions of left housing 7 and right housing 8 are removed for illustrative purposes in order to view reservoir syringe 10 and pusher 9.

As illustrated in FIG. 6, the valve 11 engages with supply syringe 110, such that supply syringe 110 is fluidly coupled with valve 11. In an embodiment, engagement between supply syringe 110 and valve 11 is a luer lock engagement. Supply syringe 110 may initially fill reservoir syringe 10 with composition and/or re-fill reservoir syringe 10 with additional composition. For example, prior to engagement of trigger 20, the user depresses a plunger of the supply syringe 110 to expel composition out of the supply syringe 110. The composition travels through the valve 11 and into the reservoir syringe 10. In this way, the reservoir syringe 10 is supplied with composition via the supply syringe 110. Consequently, as described above, engagement of trigger 20 and the entire trigger mechanism 15 causes the composition in the reservoir syringe 10 to be expelled out of the reservoir syringe 10, through the valve 11, through the cannula 23, and out of the distal end of the cannula 23.

Figure 7A:
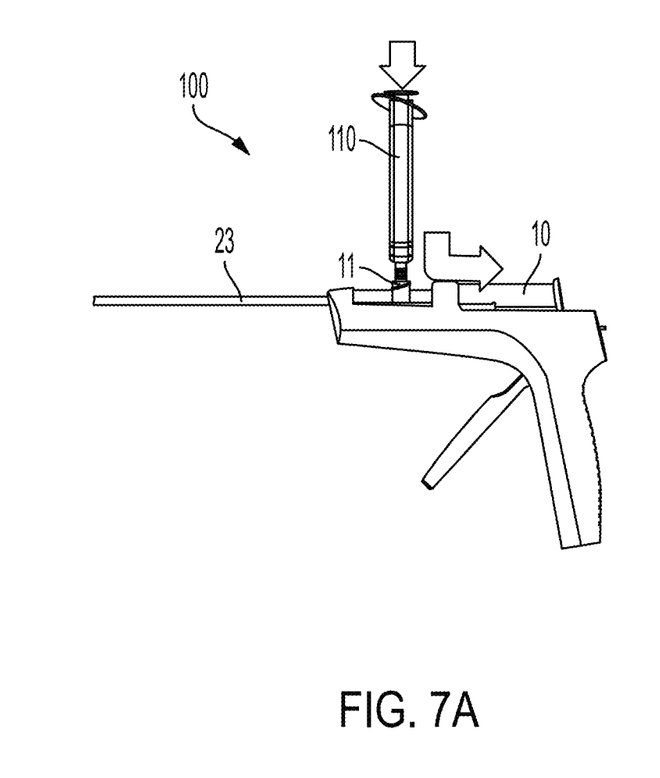
FIGS. 7A to 7B are side elevation views of a delivery system, according to an example embodiment of the present disclosure.
Figure 7B:
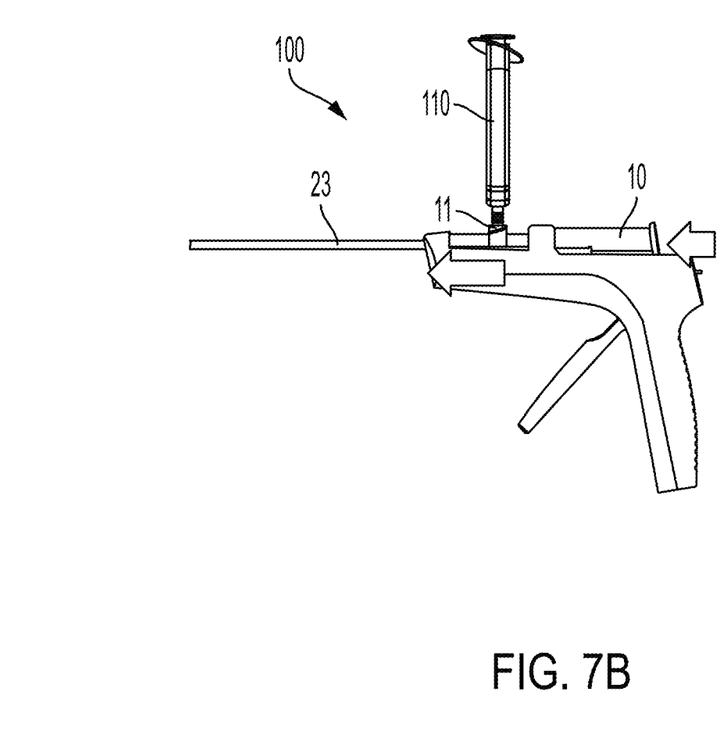

Valve 11 may be characterized as a two-way check valve. In other words, valve 11 permits two separate fluid flow paths: a first flow path and a second flow path. FIG. 7A illustrates the first flow path, which is defined from the supply syringe 110, through the valve 11, and into the reservoir syringe 10. The composition may only flow between the supply syringe 110 and the reservoir syringe 10 in the direction defined by the first flow path. One-directional flow ensures that composition will not inadvertently flow from the reservoir syringe 10, through the valve 11, and into the supply syringe 110. FIG. 7B illustrates the second flow path, which is defined from the reservoir syringe 10, through the valve 11, and into the cannula 23. The two-way check valve may advantageously remove the need for the user to manually switch flow directions, such as via a switch valve. However, in an alternate embodiment, the valve 11 may be a user-selectable stopcock valve, whereby the user can manually select which direction the composition can flow and which direction the composition cannot flow. In an embodiment, the valve 11 is configured such that the reservoir syringe 10 and the supply syringe 110 are oriented perpendicular to one another. In other embodiments, valve 11 is configured such that the reservoir syringe 10 and the supply syringe 110 are oriented parallel to one another, or any other angular orientation to one another.

To summarize, valve 11 is configured to engage with the reservoir syringe 10, such that the reservoir syringe 10 is in fluid communication with the valve 11. Cannula 23 is configured to engage with the valve 11, such that the cannula 23 is in fluid communication with the valve 11 and extends in a distal direction. Valve 11 is configured to engage with supply syringe 110, such that supply syringe 110 is in fluid communication with the valve 11. Supply syringe 110 initially includes the composition. Responsive to depressing the plunger of the supply syringe 110, the composition is expelled out of the supply syringe 110, through the valve 11, and into the reservoir syringe 10. Responsive to engagement of trigger 20, the pusher 9 and the plunger of the reservoir syringe 10 translate in the distal direction, such that the composition in the reservoir syringe 10 is expelled out of the reservoir syringe 10, through the valve 11, through the cannula 23, and out of the distal end of the cannula 23.

In an embodiment, the trigger mechanism 15 of delivery system 100 may be configured to deliver a particular amount of composition with each pull of trigger 20. For example, by knowing the distance traveled by the pusher 9 with each pull of trigger 20, and the cross-sectional area of the reservoir syringe 10, one can easily calculate the volume delivered by delivery system 100 with each pull of trigger 20. In a specific example, a half-squeeze of the trigger 20 delivers 0.5 mL of composition, whereas a full-squeeze of the trigger 20 delivers 1.0 mL of composition.

As disclosed, delivery system 100 herein provides a high degree of user control, regarding both the delivery location and the delivery rate. Delivery system 100 provides for one-handed delivery of compositions, such as hemostatic material. More specifically, single-hand positioning of the delivery device 5, and related actuation of delivery device 5 via trigger mechanism 15, improves both precision and control of hemostatic material delivery. With delivery device 5, the user can position both the delivery device 5 and the cannula 23 with a single hand, thus freeing the other hand for other purposes. The user has better control to ensure proper positioning while simultaneously delivering hemostatic material. Beyond positioning, delivery of hemostatic material is controlled from both a quantity and a rate perspective. Hemostatic material is only delivered when the trigger 20 is pulled; when the trigger 20 is pulled, only a particular amount of hemostatic material is delivered. Similarly, hemostatic material cannot be inadvertently delivered, such as by inadvertently bumping a stylet; rather, the trigger 20 must be pulled by the user to deliver hemostatic material out of cannula 23. Consistent trigger actuation will result in a consistent delivery of hemostatic material, thus preventing situations of accidental delivery, loss of product, and over-delivery, such as blowout, which can be especially problematic to the patient by causing an embolic event, flushing away previously delivered hemostatic material, or creating other undesirable side effects. Likewise, by biasing the trigger 20 to the open configuration such that engagement rack 17 and engagement pawl 16 are disengaged from pusher teeth 28, pusher 9 is free to translate backward to relieve any pressure differential remaining within reservoir syringe 10 and avoid undesirable leakage.

In an alternate embodiment, delivery system 100 and delivery device 5 may implement additional components to replace the manual and repeated trigger actuation disclosed above. For example, delivery device 5 may include electromechanical components, such as an electromechanical motor, related gearing, and a battery or external power source, such that the trigger mechanism 15 may be engaged to deliver material without requiring physical engagement of the trigger 20.

Delivery of hemostatic material via delivery device 5 and delivery system 100 also provide for mechanical optimization of the device itself. For example, trigger 20 and trigger mechanism 15 can generate a greater force when compared to previous delivery techniques, such as manual delivery via pushing a stylet through a delivery tube. With a greater delivery force available, dimensions of delivery device 5, such as the diameter of cannula 23 and size of reservoir syringe 10, can be reduced. Specifically, for example, the cannula 23 may be longer and narrower. Reducing particular dimensions of the delivery device 5, such as the diameter of the cannula 23, is a desirable whenever the delivery device 5 is to be used in endoscopic settings. For example, portions of the delivery device 5, like the cannula 23, may pass through an endoscopic port on the patient.

Furthermore, delivery device 5 and delivery system 100 provide for mechanical optimization through a "stepping down" of syringe diameters. For example, in an embodiment, the supply syringe 110 may be a 25 mL syringe. As a reminder, the user may implement the supply syringe 110 to deliver composition through valve 11, in order to supply composition to the reservoir syringe 10. The reservoir syringe 10 may be a 5 mL syringe. Because the size of the reservoir syringe 10, including the cross sectional area of the syringe, is smaller than that of the supply syringe 110, less force is required to generate pressure sufficient to expel the composition from the reservoir syringe 10. In the same vein, an equivalent force on the plunger of the supply syringe 110 will generate a higher pressure within the supply syringe 110, due to the smaller cross sectional area of reservoir syringe 10. The higher pressure is advantageous to dispense viscous compositions down a long and narrow cannula. Thus, stepping down of syringe diameters may provide for optimization of forces required to dispense viscous compositions, optimization of sizes by reducing the overall size of supply syringe 110 for a more compact delivery device 5, and the like.

Method of Administering a Hemostatic Matrix

As previously mentioned, delivery device 5 and delivery system 100 may be implemented in administering or delivering a composition. Specifically, the user may attach supply syringe 110 to the valve 11 of delivery device 5. The supply syringe 110 includes the composition to be administered, such as a viscous hemostatic matrix. Prior to attachment to the valve 11, the user may prepare the composition for administration in the supply syringe 110.

For example, when a hemostatic matrix, such as FLOSEAL®, is to be administered, the FLOSEAL® must first be prepared for administration. FLOSEAL® VH S/D may be prepared according to the manufacturer's Instructions for Use (Baxter Healthcare Corporation, 2014). Particularly, a thrombin solution may be prepared by attaching a prefilled sodium chloride solution syringe to a luer connector of a vial adapter containing the thrombin solution. The rubber stopper of the thrombin vial is pierced, and all contents of the sodium chloride syringe are transferred to the thrombin vial. The thrombin vial is then vented and swirled until the thrombin is completely dissolved. FLOSEAL® VH S/D is then prepared by filling an empty 10 mL supply syringe 110 with thrombin solution to an indicated mark, such as 8 mL, and then connecting a gelatin matrix syringe to the supply syringe 110 containing the thrombin solution. The thrombin solution is then passed into the gelatin matrix syringe, and the mixture transfers back and forth between the two syringes for at least twenty passes. The resulting hemostatic matrix in the supply syringe 110 is ready for administration, typically between thirty seconds and twenty minutes after preparation.

Once the hemostatic matrix is prepared, the user attaches supply syringe 110 containing the hemostatic matrix to the valve 11 of delivery device 5. In a preferred embodiment, the reservoir syringe 10 is initially empty and the plunger of reservoir syringe 10 is initially compressed. The user then depresses a plunger of the supply syringe 110 such that, responsive to depressing the plunger, the hemostatic matrix is expelled out of the supply syringe 110, through the valve 11, and into the reservoir syringe 10. In an embodiment, the user only expels a portion of the supply syringe 110 into the reservoir syringe 10. For example, the supply syringe 110 may have a much larger volume capacity than the reservoir syringe 10.

The user then repeatedly engages the trigger mechanism 15, specifically the trigger 20, of delivery device 5 such that, responsive to engaging the trigger mechanism 15, a plunger of the reservoir syringe 10 is depressed. For example, the pusher 9 translates in a distal direction to depress the plunger of reservoir syringe 10. The hemostatic matrix is expelled out of the reservoir syringe 10, through the valve 11, and into the cannula 23.

The user then further depresses the plunger of supply syringe 110, such that additional hemostatic matrix is expelled out of the supply syringe 110, through the valve 11, and into the reservoir syringe 10. For example, the user has the capability to re-load reservoir syringe 10 with additional hemostatic matrix. During reloading, components of the trigger mechanism 15 may reset and other components, such as the pusher 9 and the plunger of reservoir syringe 10 may translate in the proximal direction as the reservoir syringe 10 is filled with additional hemostatic matrix.

The user then further repeatedly engages the trigger mechanism 15, specifically the trigger 20, of delivery device 5 such that, responsive to engaging the trigger mechanism 15, the plunger of the reservoir syringe 10 is depressed and additional hemostatic matrix is expelled out of the reservoir syringe 10, through the valve 11, and into the cannula 23. By repeating this process, hemostatic matrix is expelled out of the tip 27 of cannula 23.

If the user runs out of hemostatic matrix in the supply syringe 110, the user may detach the empty supply syringe 110 from the valve 11 and attach a new supply syringe 110 to the valve 11 to continue the process. This may advantageously improve both preparation time associated with readying the delivery device 5 and reload time associated with reloading the delivery device 5 with additional hemostatic matrix.

In a related embodiment, delivery device 5 may include a liquid propellant for expelling material out of the tip 27 of cannula 23. For example, in this embodiment, the reservoir syringe 10 is initially empty and the plunger of reservoir syringe 10 is initially compressed. As previously described, the user depresses a plunger of the supply syringe 110 such that, responsive to depressing the plunger, the hemostatic matrix is expelled out of the supply syringe 110, through the valve 11, and into the reservoir syringe 10. The user then repeatedly engages the trigger mechanism 15, specifically the trigger 20, of delivery device 5 such that, responsive to engaging the trigger mechanism 15, a plunger of the reservoir syringe 10 is depressed. The hemostatic matrix is expelled out of the reservoir syringe 10, through the valve 11, and into the cannula 23.

At this point, the user may attach a second supply syringe, such as a liquid filled syringe, to valve 11. The user depresses a plunger of the second supply syringe such that, responsive to depressing the plunger, liquid is expelled out of the second supply syringe, through the valve 11, and into the reservoir syringe 10. For example, the user has the capability to load reservoir syringe 10 with liquid, after delivery of hemostatic material into cannula 23. During loading with liquid, components of the trigger mechanism 15 may reset and other components, such as the pusher 9 and the plunger of reservoir syringe 10 may translate in the proximal direction as the reservoir syringe 10 is filled with liquid. The user further repeatedly engages the trigger mechanism 15, specifically the trigger 20, of delivery device 5 such that, responsive to engaging the trigger mechanism 15, the plunger of the reservoir syringe 10 is depressed and the liquid is expelled out of the reservoir syringe 10, through the valve 11, and into the cannula 23. In this way, the liquid acts as a pressurized propellant and expels the hemostatic material out of the tip 27 of cannula 23.

In a different related embodiment, all components of the delivery device 5 are stainless steel and can be configured for repeated use. For example, delivery device 5 may be used as described above, and may subsequently be sterilized via an autoclave or other commercial sterilizer. Once sterilized, delivery device 5 could effectively be reused at a later date for delivering hemostatic matrix to a different patient.

Flushing Method

The delivery device 5 and delivery system 100 may further advantageously reduce wasted material associated with incomplete delivery. For example, the method described above may further include a flushing operation. Specifically, once the user is finished with expelling hemostatic matrix out of the tip 27 of cannula 23, a holdup volume of hemostatic matrix remains unused in the cannula 23. In this situation, the user may detach the supply syringe 110 from the valve 11 of delivery device 5. The user then attaches a flush syringe to the valve 11 of delivery device 5.

The flush syringe includes a flushing fluid, which is different from the hemostatic matrix. For example, the flushing fluid may be liquid saline, or other liquid medium, or gas. Once the flush syringe is attached to valve 11, the user depresses a plunger of the flush syringe, such that the flushing fluid is expelled out of the flush syringe, through the valve 11, and into the reservoir syringe 10. The user may then engage the trigger mechanism 15, such that the plunger of the reservoir syringe 10 is depressed to expel the flushing fluid out of the reservoir syringe 10, through the valve 11, and into the cannula 23. In this way, the flushing fluid, and the associated pressure generated by the flushing fluid, expels any remaining hemostatic matrix out of the cannula 23.

The flushing operation provides for optimal delivery of the hemostatic matrix, minimizing the waste of hemostatic matrix remaining in the cannula 23. The flushing operation further eliminates clogging, by minimizing the amount of hemostatic material that remains in the cannula 23.

Delivery Device Kit

Kits according to the present disclosure may comprise the hemostatic material and a delivery device 5. The hemostatic materials are formed sterilely, by aseptic processing, or will be sterilized, preferably by terminal sterilization using γ-irradiation, ethylene oxide, electronic beam irradiation, and the like. While still in a sterile form, the hemostatic materials will be packaged in a sterile package, such as a pouch, tube, tray, box, or the like. Instructions for use setting forth a method of placing the material over tissue in the presence of blood at a wound, or surgical site, may also be provided as part of the kit. An exemplary kit includes the hemostatic material, such as dry bovine-derived gelatin matrix (granules) and a human-derived thrombin solution in individual syringes, an applicator tip, a delivery device described herein configured to be used with the syringe, and instructions for use setting forth methods for inhibiting bleeding by placing the sterilized materials at a target site in tissue, which could be any wound or other site of bleeding tissue, with a delivery device or delivery system, such as those disclosed herein.

In an embodiment, a kit includes a pre-filled sodium chloride solution syringe, a thrombin vial, a pre-filled gelatin matrix syringe, and a delivery device. The pre-filled sodium chloride solution syringe, thrombin vial, and pre-filled gelatin matrix syringe may be used to prepare a hemostatic matrix as described above. The delivery device 5 may be configured to engage with the pre-filled gelatin matrix supply syringe 110 as described in greater detail above.

As used in this specification, including the claims, the term "and/or" is a conjunction that is either inclusive or exclusive. Accordingly, the term "and/or" either signifies the presence of two or more things in a group or signifies that one selection may be made from a group of alternatives.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention claimed is:

1. A delivery device comprising:
   a trigger mechanism;
   a pusher, configured to engage with the trigger mechanism, the pusher further configured to retain a first syringe at least by coupling with a plunger of the first syringe;
   a valve fluidly coupled to the first syringe; and
   a cannula extending distally from and fluidly coupled to the valve, wherein the cannula includes an inner cannula configured to deliver a composition and an outer cannula, the outer cannula disposed concentrically around the inner cannula,
   wherein activation of the trigger mechanism causes the pusher and the plunger of the first syringe to translate in a distal direction, such that the composition in the first syringe is expelled out of the first syringe, through the valve, through the inner cannula, and out of a distal end of the inner cannula, and wherein the valve is further configured to engage with a second syringe, such that the second syringe is in fluid communication with both the valve and the first syringe, and wherein the valve is a two-way check valve that permits a flow through a first flow path from the second syringe to the first syringe and a second flow path from the first syringe to the inner cannula, wherein the composition is a viscous hemostatic material.

2. The delivery device of claim 1, wherein prior to activation of the trigger mechanism, the composition is expelled out of the second syringe, through the valve, and into the first syringe, such that the first syringe is filled with the composition via the second syringe.

3. The delivery device of claim 1, wherein engagement between the valve and the second syringe is a luer lock engagement.

4. The delivery device of claim 1, wherein the pusher includes a plurality of teeth, and wherein the trigger mechanism includes a ratchet, the ratchet configured to engage with the plurality of teeth of the pusher.

5. The delivery device of claim 1, further including a window indicator that indicates an amount of the composition remaining in the first syringe.

6. The delivery device of claim 1, wherein the outer cannula is stainless steel.

* * * * *